United States Patent [19]

Steigerwald

[11] 4,109,651
[45] Aug. 29, 1978

[54] ANESTHETIC GAS EXHAUST SYSTEM

[76] Inventor: Allan M. Steigerwald, 9860 SW. Eagle La., Beaverton, Oreg. 97005

[21] Appl. No.: 633,225

[22] Filed: Nov. 19, 1975

[51] Int. Cl.$^2$ ............................................ A61M 16/00
[52] U.S. Cl. ............................... 128/145.8; 128/145.7
[58] Field of Search ................. 128/188, 145.6, 145.7, 128/195.8, 202, DIG. 5, 351, 350 V; 251/342

[56] References Cited

U.S. PATENT DOCUMENTS

| | | | |
|---|---|---|---|
| 3,105,488 | 10/1963 | Richards | 128/145.7 |
| 3,469,582 | 9/1969 | Jackson | 128/276 |
| 3,473,531 | 10/1969 | Tatham | 128/202 |
| 3,774,591 | 11/1973 | Corbin | 128/DIG. 5 |
| 3,785,377 | 1/1974 | Jorgensen | 128/188 |
| 3,800,793 | 4/1974 | Marrese | 128/188 |

FOREIGN PATENT DOCUMENTS

| | | | |
|---|---|---|---|
| 2,213,764 | 9/1973 | Fed. Rep. of Germany | 128/188 |
| 993,971 | 6/1965 | United Kingdom | 251/331 |

*Primary Examiner*—Robert W. Michell
*Assistant Examiner*—Henry J. Recla
*Attorney, Agent, or Firm*—Francis Swanson

[57] ABSTRACT

A system for controlling anesthetic gases exhausting from anesthetic administering equipment is disclosed. The system is designed so as to regulate the anesthetic gases in a manner which isolates gases and prevents them from escaping into the operating room atmosphere. A manually controllable valve having a rubber diaphragm to control the flow of gases exhausted from the system is disclosed.

6 Claims, 3 Drawing Figures

U.S. Patent  Aug. 29, 1978  4,109,651
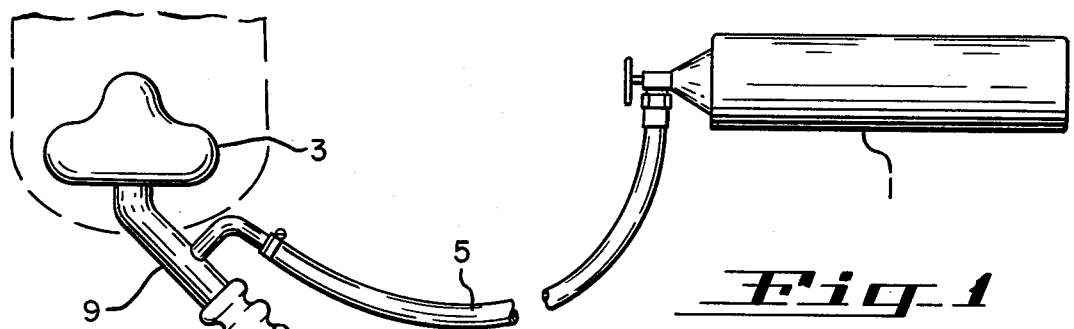
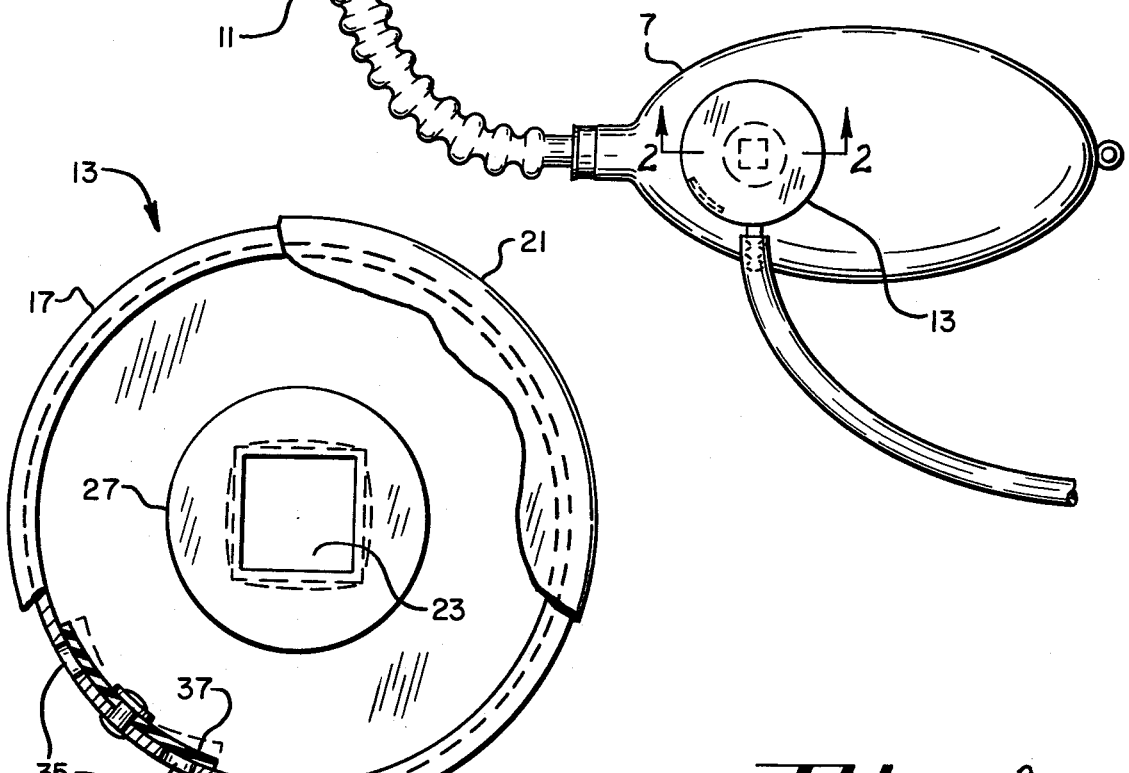
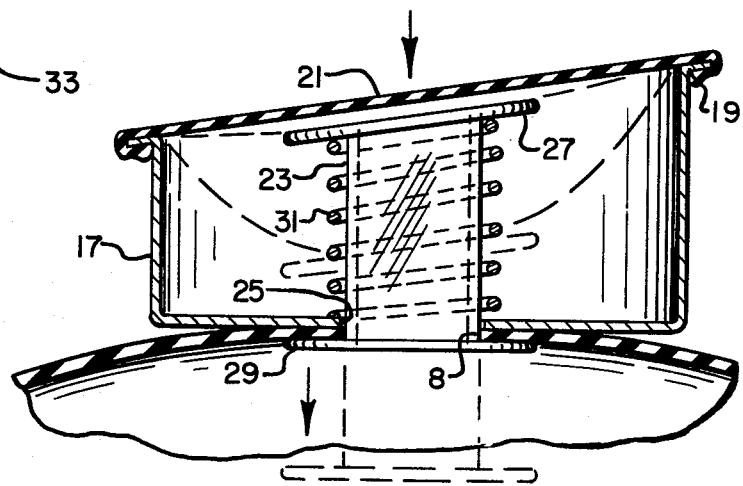

ANESTHETIC GAS EXHAUST SYSTEM

BACKGROUND OF THE INVENTION

1. Field of the Invention

The present invention relates to systems for administering anesthetic gases in general and more particularly to those systems having means for exhausting the anesthetic gases in a manner which prevents pollution of the operating room atmosphere.

2. Description of the Prior Art

Numerous anesthetic gas administering systems exist in the prior art. Devices may be either rebreathing or nonrebreathing types. A typical system consists of an anesthesia machine to provide fresh gases to a patient. The machine is operatively connected to the patient via breathing tubes and a face mask. Appropriate one-way valving is provided in the breathing tubes and the system usually contains a gas reservoir such as a breathing bag. The breathing bag may be used by the physician to assist the patient in breathing by rhythmically squeezing the bag. Some breathing bags contain a small vent hole in one side. Others have a small open nipple extending from the end of the bag which may be pinched off. In operation, the physician will open or close this vent hole with his thumb or finger to regulate the volume and pressure within the breathing bag. When the hole in the bag is uncovered and anesthetic gases inevitably escape into the operating room atmosphere, these escaping gases may have an adverse effect on on operating room personnel, particularly after long or frequent exposure.

SUMMARY OF THE INVENTION

In accordance with the present invention, a manually controllable valve is placed in the side vent hole of the breathing bag and provides means whereby anesthetic gases may be exhausted from the gas administering system and out of the operating room or into a closed container while controlling the flow and simultaneously prohibiting any escape of residual gases into the operating room atmosphere.

A principal object of the invention is to provide a system for administering anesthetic gases which prohibits the escape of residual gases into the operating room atmosphere.

A further object of the invention is to scavenge anesthetic gases and vapors as they exit from the breathing bag and evacuate such gases in a controlled manner.

A further object of the invention is to provide manually controllable means for regulating the pressure and volume of gases in the breathing bag while simultaneously controlling the flow of exhaust gases out of the operating room in a closed system under normal conditions.

DESCRIPTION OF THE DRAWINGS

The foregoing and other features, objects and advantages of the invention will be more apparent from the following detailed description which proceeds with reference to the accompanying drawings, wherein:

FIG. 1 shows a typical nonrebreathing anesthetic gas administering system having a manually controllable valve attached to the breathing bag.

FIG. 2 is a sectional view taken along Line 2—2 of FIG. 1.

FIG. 3 is a plan view of the manually controllable valve partially broken away to show the interior details thereof.

DETAILED DESCRIPTION

Referring now to the drawings, FIG. 1 shows a source of anesthetic gas 1 which is operatively connected to a face mask 3 via gas supply tube 5. As an alternative to the face mask an endotracheal tube or other suitable device could be used. Face mask 3 is connected to breathing bag 7 via a metal fitting 9 and a flexible breathing tube 11. A manually controllable valve 13 is operatively connected to breathing bag 7 through the vent hole 8 in the bag. Valve 13 is attached to an exhaust gas hose 15 which leads uninterrupted to an exit or external vent source, usually a suction system, outside the operating room. As used here, "outside the operating room" is understood to mean an actual vent which carries the gas to a location physically outside the room or to a closed reservoir or collection system located within the operating room. The important point is that with the system as disclosed the gases are isolated from escape into the operating room atmosphere under normal conditions.

Valve 13 is connected to breathing bag 7 through bag vent hole 8 as shown in FIG. 2. The valve consists of a cylindrically shaped hollow body 17. Body 17 is open at the top and defines an outwardly protruding lip 19 at its upper edge. A flexible diaphragm 21 made of a suitable elastomer and having a lip at its outer perimeter encloses the upper end of body 17. A slideable gas inlet port 23 is mounted within valve body 17 and protrudes through hole 25 in the bottom of body 17. Inlet port 23 has an upper flange 27 and a lower flange 29 and is open throughout its entire length to provide a passageway for the flow of exhaust gases from bag 7 into the interior of body 17. Inlet port 23 is moveable along its longitudinal axis and spring-loaded within body 17 by spring 31. This spring 31 must provide a large measure of upward bias in order to clamp and seal bag 7 as will be explained below. A gas exit port 33 consisting of a slightly tapered tubular flange is mounted on body 17 A plurality of ports 35 are cut into the side of body 17. These ports are sealed from the inside with an elastomer flapper 37.

OPERATION

Valve body 17 is mounted on breathing bag 7 by pressing downward on the upper end of port 23 at flange 27 and forcing flange 29 through the side vent hole 8 of bag 7. After release of downward pressure on slideable port 23 the force of spring 31 compresses the edges of vent hole 8 of bag 7 between flange 29 and the bottom side of valve body 17, thus effectively sealing the side hole of the bag. Tube 15 is connected to exhaust port 33 of valve 13 and attached to an exterior vent which is usually a suction system (not shown). Breathing bag 7 is connected to face mask 3 via tube 11, fitting 9, and to the source of gas 1 via Line 5. Face mask 3 is placed upon patient's face and the source of gas turned on. The system is now ready for use. As the patient breaths, exhaled anesthetic gas and vapors move from the face mask 3 down through tube 11 and into breathing bag 7. Gas flowing into bag 7 flows upward through inlet port 23 into the interior of valve body 17 and on out through exit port 33, tube 15, and out of the operating room or into an alternate closed collection system. Now, if the physician wishes to increase the pressure and/or volume of anesthetic gases in breathing bag 7, he merely presses a finger downward upon flexible diaphragm 21, either partially or completely, closing off the upper end of inlet port 23 throttling the flow of exhaust gases out of the system. Closing off the flow of gas from out of the system will result in an increase in volume and pressure within bag 7. The physician may assist the patient in breathing by rhthymically squeezing the bag 7. He may simultaneously control the volume and pressure in the bag 7 by manually pressing diaphragm 21 against all or part of the upper end of inlet port 23. Fingertip control of the flow of gases exhausted from the system is thus provided.

In the event that negative pressure develops in valve body 17, collapse of bag 7 is prevented, as the drop in pressure in the interior of valve body 17 will cause flapper 37 to move away from ports 35 and air from the operating room atmosphere will flow into valve body 17 through holes 35. In an alternate construction without ports 35 and flapper 37 development of negative pressure in body 17 will cause diaphragm 21 to collapse against gas inlet port 23 and seal off the flow of gas.

Having described the preferred embodiment of my invention, it will be apparent to those skilled in the art that modifications and changes could be made in the design without departing from the spirit and scope of my invention.

Therefore, I claim as my invention all such embodiments as fall within the scope of the appended claims.

1. Apparatus for administering anesthetic gases to a patient comprising:
    a source of gas;
    means operatively connected to the gas source for introducing the gas to the patient's respiratory system;
    a breathing bag connected to the gas introducing means, one wall of the bag defining a gas exit hole; and
    a manually operable variable gas exit valve including a housing having a gas inlet port and flow control means operable against the inlet port and variable through operator finger pressure for controlling flow between said gas and said gas exit port, said gas inlet port being detachably mounted on the bag by connection through the hole, the gas exit port being connected to an external vent source whereby an operator may continuously regulate the flow of gas from the apparatus to the external vent source by depression, through operator finger pressure, of the flow control means against the gas inlet port when the apparatus is in operation.

2. Apparatus according to claim 1 wherein the valve comprises:
    a hollow body defining a cavity having an open top, a surrounding wall and a bottom; a gas inlet port and a gas exit port connected to the external vent source and;
    an external elastic diaphragm mounted in closing relation on the open top of the body, the diaphragm compressible against the gas inlet port by contact with an operator's finger to throttle the flow of gas from the inlet port upon application of external pressure to the diaphragm.

3. Apparatus for administering anesthetic gases to a patient comprising:
    a source of gas;
    means operatively connected to the gas source for introducing gas into the patient's respiratory system;
    a breathing bag operatively connected to the gas introducing means, one wall of the bag defining a gas exit hole;
    a manually operable gas exit control valve including a housing having gas inlet means and a gas exit port, the valve detachably mounted on the breathing bag by insertion of the gas inlet means into the breathing bag gas exit hole, said gas exit port also connected to an external vent source, the bag, valve and vent source forming a continuous closed gas exit path which isolates the gas from the surrounding atmosphere, the manually operable valve including an external diaphragm positioned transversely of said gas inlet means and, the diaphragm depressable by the finger of an operator against the gas inlet means within the valve to optionally vary the flow of gases exiting from the apparatus while the gases are simultaneously isolated from escape into the surrounding atmosphere.

4. Apparatus for administering anesthetic gas to a patient comprising:
    a source of gas;
    means operatively connected to the gas source for introducing gas into a patient's respiratory system;
    a breathing bag operatively connected to the gas introducing means and having a hole in the wall thereof;
    a manually operable gas exit flow control valve detachably mounted on the breathing bag by connection to said hole in the wall of the bag and to an external vent source, the manually operable valve defining a chamber which is open at one end, the chamber having a gas inlet port which protrudes through the hole in the breathing bag, said gas inlet port extending within the chamber to a point adjacent the chamber's open end, the chamber also having a gas outlet port, a tube connecting said gas outlet port to an external vent source, the bag, the valve, the tube and vent source forming a continuous closed path which isolates exiting gas from within the apparatus from the surrounding atmosphere;
    and a removable external elastic diaphragm mounted across the open end of the chamber adjacent and above the gas inlet port so as to close the chamber from the surrounding atmosphere, the diaphragm optionally and variably compressible by direct pressure of the hand of an operator against the diaphragm to force said diaphragm against the gas inlet port to throttle the flow of gases from the bag to the external vent source while the gases are isolated from escape into the surrounding atmosphere while passing to the external vent source.

5. Apparatus according to claim 4 wherein the valve includes an elastic negative pressure relief diaphragm on the inner wall of the chamber adapted to admit air from the surrounding atmosphere into the apparatus whenever pressure within the chamber drops below the pressure in the surrounding atmosphere.

6. An overflow gas discharge control and exhaust system for a non-rebreathing apparatus of the type including a breathing bag formed of a resiliently deformable material and provided with a bleed opening in a wall thereof sized to be blocked by the thumb of an apparatus operator, said system comprising in combination:
    an operator thumb actuated valve device including a body adapted to be fixed to said breathing bag within said bleed opening and an actuator fixed to said body, said body including a bottom wall, a base portion depending from said bottom wall and cooperating therewith to define an annular groove, said groove receiving portions of said wall of said bag peripherally bounding said bleed opening in a resilient manner and in fluid sealed relationship, a cylindrical side wall upstanding from said bottom wall, a pedestal portion upstanding from said bottom wall and disposed concentrically inwardly of said side wall, said bottom and side walls cooperating to define a cavity bounding said pedestal portion and having an open end bounded by a rim portion of said side wall, said rim portion forming an outwardly opening annular shoulder, said pedestal portion defining a valve seat arranged within and normally communicating with said cavity, an inlet passageway extending from said valve seat through said pedestal portion and said bottom wall and said base portion for placing said valve seat in flow communication with said breathing bag when said body is fixed thereto, an outlet passageway extending through said side wall of communication with said cavity, and said actuator is in the form of a disc shaped diaphragm formed of resiliently deformable material and having a peripherally extending bead snap fitted over said annular shoulder of said rim portion whereby to fix said diaphragm to said side wall for closing said open end of said cavity, said diaphragm tending to assume a rest position spaced from said valve seat and being deformable by application of operator thumb pressure thereto to assume an operative position in engagement with said valve seat, whereby to block flow communication between said cavity and said inlet passageway; and a flexible tube fixed to said outlet passageway for flow communication with said cavity, said tube being of a length sufficient to exhaust gas passing from said breathing bag through said valve device at a point relatively remote from said bleed opening.

* * * * *